(12) United States Patent
Brabrand

(10) Patent No.: US 8,814,793 B2
(45) Date of Patent: Aug. 26, 2014

(54) RESPIRATION MONITOR

(75) Inventor: Knut Brabrand, Rasta (NO)

(73) Assignee: Neorad AS, Oslo (NO)

( * ) Notice: Subject to any disclaimer, the term of this patent is extended or adjusted under 35 U.S.C. 154(b) by 3489 days.

(21) Appl. No.: 10/725,431

(22) Filed: Dec. 3, 2003

(65) Prior Publication Data

US 2004/0167389 A1 Aug. 26, 2004

Related U.S. Application Data

(60) Provisional application No. 60/430,676, filed on Dec. 4, 2002.

(30) Foreign Application Priority Data

Dec. 3, 2002 (GB) .................................. 0228189.7

(51) Int. Cl.
*A61B 8/00* (2006.01)

(52) U.S. Cl.
USPC ........................................................ 600/437

(58) Field of Classification Search
None
See application file for complete search history.

(56) References Cited

U.S. PATENT DOCUMENTS

| | | | | |
|---|---|---|---|---|
| 3,993,995 | A | 11/1976 | Kaplan et al. | 343/7 ED |
| 4,122,427 | A | 10/1978 | Karsh | 340/1 R |
| 4,431,007 | A * | 2/1984 | Amazeen et al. | 600/440 |
| 4,915,103 | A | 4/1990 | Visveshwara et al. | 128/204.23 |
| 5,220,922 | A | 6/1993 | Barany | 128/660.01 |
| 5,224,175 | A * | 6/1993 | Gouge et al. | 382/128 |
| 5,355,887 | A * | 10/1994 | Iizuka et al. | 600/440 |
| 5,363,844 | A * | 11/1994 | Riederer et al. | 600/413 |
| 5,448,995 | A | 9/1995 | Yost et al. | 128/660.07 |
| 5,839,442 | A * | 11/1998 | Chiang et al. | 600/447 |
| 6,110,112 | A | 8/2000 | Heywang-Koebrunner | |
| 6,144,875 | A * | 11/2000 | Schweikard et al. | 600/427 |
| 6,298,260 | B1 * | 10/2001 | Sontag et al. | 600/413 |

(Continued)

FOREIGN PATENT DOCUMENTS

| | | |
|---|---|---|
| EP | 0 324 275 A1 | 7/1989 |
| EP | 0 940 158 A1 | 9/1999 |
| EP | 1 086 652 A1 | 3/2001 |
| EP | 1 208 796 A1 | 5/2002 |
| WO | 02/41776 A1 | 5/2002 |

OTHER PUBLICATIONS

Houston et al., Ultrasound assessment of normal hemidiaphragmatic movement: relation to inspiratory volume, Jan. 24, 1994, Thorax 1994;49:500-503.*

(Continued)

*Primary Examiner* — Peter Luong

(74) *Attorney, Agent, or Firm* — Finnegan, Henderson, Farabow, Garrett & Dunner, L.L.P.

(57) ABSTRACT

A respiration monitor comprises a transducer array 5 having a plurality of individual transducer elements 7 that span at least part of the region of diaphragm movement of a patient. A patient 1 having a lung 2 and an abdomen 3 being separated therefrom by a diaphragm 4 is fitted with an ultrasound transducer array 5 over the lung sinus 6 prior to being given a CT or MRI scan. Each individual transducer element 6 emits an ultrasound pulse and then detects its echo in the known manner. Because air has a much higher acoustic impedance than tissue, the reflection of the ultrasound beam is much more pronounced when the lung is insonated.
By measuring the strength of the receiving signal, it is possible to determine to a high degree of accuracy the position of the patient's diaphragm.

20 Claims, 4 Drawing Sheets

(56) References Cited

U.S. PATENT DOCUMENTS

| | | | |
|---|---|---|---|
| 6,314,312 B1 * | 11/2001 | Wessels et al. | 600/427 |
| 6,346,079 B1 * | 2/2002 | Haider et al. | 600/443 |
| 6,405,072 B1 * | 6/2002 | Cosman | 600/426 |
| 6,937,696 B1 * | 8/2005 | Mostafavi | 378/95 |
| 6,937,883 B2 * | 8/2005 | Prince | 600/411 |
| 2002/0115923 A1 | 8/2002 | Erbel | 600/407 |

OTHER PUBLICATIONS

XP-002273267, M. Kokubo et al., Non-Invasive Respiratory-Gated Radiation Treatment System Based on a 3-D Ultrasound Device and a 3-D Digital Localizer I, J. Radiation Oncology˙Biology˙Physics, vol. 54, No. 2, Supplement, 2002.

* cited by examiner

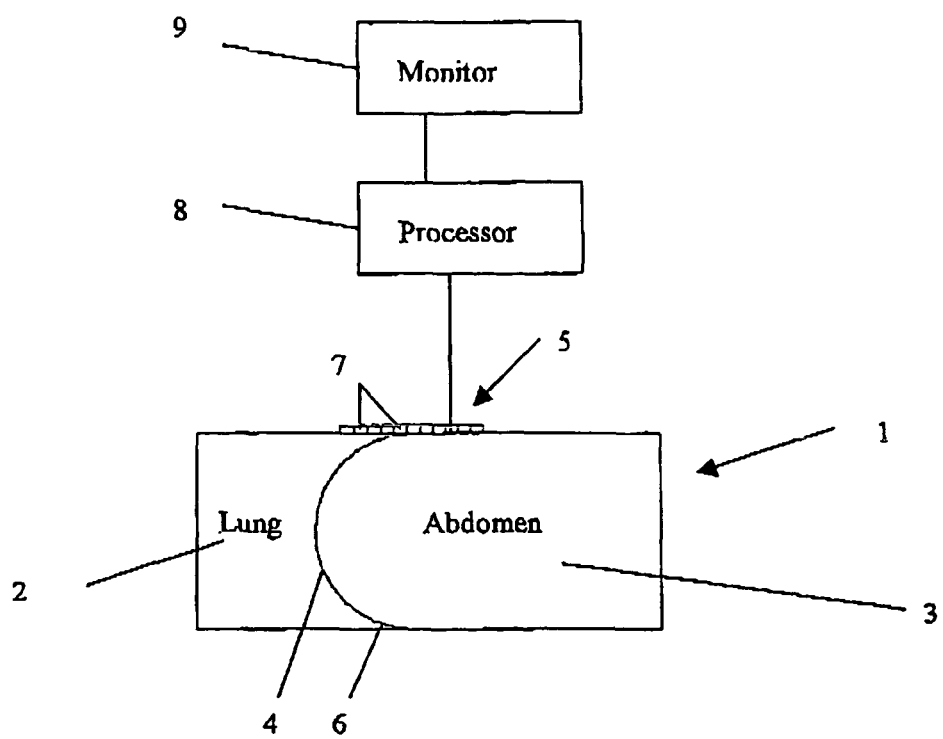

RESPIRATION MONITOR

CROSS REFERENCE TO RELATED APPLICATIONS

This application claims the benefit of U.S. Provisional Application No. 60/430,676, filed Dec. 4, 2002, the content of which is incorporated herein by reference, and claims the right to priority based on United Kingdom Application No. 0228189.7, filed Dec. 3, 3002.

The present invention relates to a non-invasive method and apparatus for monitoring the degree of inspiration of a medical or surgical patient's lungs.

In many circumstances (e.g. when performing biopsies or radiotherapy), it is desirable to precisely locate a target area of a lung or of an organ in the upper abdomen. For example, in order to perform a lung biopsy, pre-operative CT images may be generated. These are then used to determine how the biopsy needle should be inserted in order to reach its target. After the needle has been inserted, fresh CT images may be generated in order to check the position of the needle. If necessary, this can then be corrected and the procedure repeated in an iterative manner.

During such a CT guided puncture, several parameters are of great importance in order to hit the target, e.g. insertion of the needle with the correct angle, needle deflection at various tissue interfaces and patient cooperation, including respiratory control. Lesions in the lungs, particularly in the lower parts, and also in the upper abdominal area move with respiration. The degree of respiratory movement is greater in the lower parts of the lung and the upper part of the abdomen. Other organs and tissues move to some extent with respiration.

Although some x-ray based imaging techniques can be used in real-time, it is not desirable to continuously monitor a biopsy using x-rays because of the well known risks associated with exposure to such radiation. Magnetic implements cannot be used during MRI scans because of the high magnetic field used.

Conventionally, the patient is asked to hold his breath when the CT scan takes place. He is then asked to hold his breath at the same level of inspiration during puncture. However, it will be appreciated that it is difficult for the patient to reproduce the same degree of inspiration. Consequently, the images may not accurately reflect the position of the target within the patient. Thus, an objective means of monitoring the level of inspiration could improve the puncture accuracy because the operator would have better control over the movement of the target along the longitudinal body axis (the z-direction).

U.S. Pat. No. 6,110,112 discloses a medical guide apparatus for breath-coordinated puncturing of the body. In this apparatus, a reference point is located which will be visible in both an ultrasound scan and in an MRI or CT scan. The arrangement is such that the location of the reference point will vary with respiration in the same manner as the target point. The target (which shows up in only the MRI or CT scan) can then be located by calculating its position relative to the reference point. The practitioner must calculate the relative displacements in the x, y and z-axes of the target point from the reference point.

The apparatus of U.S. Pat. No. 6,110,112 consists of an ultrasound applicator with a puncture instrument attached thereto. The relative displacement between the ultrasound applicator and the puncture instrument is variable. The practitioner therefore sets the relative displacement of the puncture instrument from the ultrasound applicator such that the puncture instrument is directed at the target. Then, the practitioner locates the reference point with the ultrasound applicator and performs the puncture. This method requires that the reference point used moves in exactly the same way as the target area throughout the respiration cycle. It also requires a cumbersome apparatus to be mounted above the patient after the CT or MRI scan has been performed.

There is a similar problem of z-direction movement associated with radiation therapy of a tumor. If the tumor is in the lung or upper part of the abdomen, it may move in and out of the focus of the radiation beam as the lungs expand and contract. The current method of overcoming this problem is to choose the area to be irradiated to be large enough to cover the tumor during its respiratory movement. This inevitably results in the irradiation of non-cancerous tissue. The inventors have therefore recognized that a device that can monitor and send information about the respiration to a radiation unit would be desirable. This could enable a radiation unit to map the radiation beam as a function of the patient respiration and thus trigger the radiation unit to only radiate when the tumor is in focus.

SUMMARY

According to the invention there is provided a method of determining the degree of lung inspiration in a patient comprising the step of non-invasively detecting the position of the patient's diaphragm.

Thus, the invention is based on the recognition that the diaphragm provides an effective and measurable reference point that may be used to define lung inspiration.

The invention may thus be used to assist in image-guided procedures as discussed above. The diaphragm position may therefore be used to define the degree of lung inspiration when an image of the patient is generated and the method may further comprise the step of reproducing that degree of lung inspiration in order to perform a medical or surgical procedure on the patient based on that image.

For example, diaphragm position may first be determined and then, whilst the patient holds his breath, images may be generated. Subsequently, the degree of lung inspiration may be substantially reproduced by the patient inhaling until the previously determined diaphragm position is achieved. The desired procedure is then carried out whilst the patient holds his breath.

Although diaphragm position could be determined using a number of techniques, particularly non-invasive imaging techniques, it is preferred to use ultrasound. This does not subject the patient to ionizing radiation and is convenient to use. Although ultrasound cannot image certain body structures it provides a very effective way to determine the position of the diaphragm.

A conventional hand-held ultrasound probe could be used to scan the patient's abdomen. However, this would still require a reference point to define the diaphragm's position and it would be difficult to monitor movement of the diaphragm.

Thus, according to a preferred aspect of the invention there is provided a method of monitoring the degree of lung inspiration in a patient comprising providing an array of ultrasound transducer elements on the patient extending over the lung sinus, wherein the position of the diaphragm is determined based upon the signals received by the individual transducer elements.

The invention makes use of the fact that air has a very high acoustic impedance compared to non-aerated tissue (tissue not containing air). During inspiration, as the lung expands downwards and fills with air, the lung sinus opens up. The acoustic impedance of the lung sinus is thus increased. The opposite takes place during expiration. As a consequence, transducer elements located adjacent to aerated tissue will provide very distinct outputs compared to those adjacent to non-aerated tissue. In this way the invention allows accurate real time monitoring of the position of the diaphragm.

As the transducer elements are adapted to extend over the lung sinus, they may extend from the upper abdomen of a patient to the lower chest, the upper abdomen and the lower chest meeting at the lung sinus and being divided from one another by the diaphragm.

The invention also extends to an apparatus for performing such a method and therefore, viewed from another aspect, the invention provides an apparatus for monitoring the degree of lung inspiration in a patient comprising an array of ultrasound transducer elements for placing on the patient to extend over the lung sinus, wherein the position of the diaphragm may be determined based upon signals received by the individual transducer elements.

The array preferably comprises a series of ultrasound transducer elements (more preferably low cost disposable transducer elements) that is placed in a line in the z-direction over the lung sinus. The array is preferably fixed to the patient's skin in a lower intercostal space using an adhesive. In accordance with standard practice, a coupling medium (ultrasound gel) should preferably be applied to the patient's skin under the transducer elements.

In preferred forms of the invention the transducer array may indicate its own proper placement by giving feedback to the user. Thus, in one preferred method, the array of ultrasound transducer elements is placed over the patient's lower chest and/or upper abdomen and is moved to a desired location over the lung sinus using feedback from the ultrasound transducer elements.

In one preferred embodiment, the array of transducer elements is made long enough to extend across the full extent of movement of a patient's diaphragm, i.e. to cover a patient's full breathing range. In an alternative embodiment however, the array of transducer elements may be shorter than the full breathing range of a patient, so as for example to cover 50% of a patient's full breathing range. In one possible embodiment, a single transducer element could be used rather than an array but this would require cooperation from a patient to hold their breath while the diaphragm was located and the transducer element positioned thereon. Further, it is believed that the use of a single transducer element would not be as accurate as it would be very difficult to position the transducer element directly on the edge of the diaphragm. More preferably therefore, at least two transducer elements are used. This has the advantage that a transducer element can be placed on either side of the diaphragm to give a user the certainty that the diaphragm is located between the two elements when the difference in reading obtained by the two elements is sufficiently high.

Although the transducer array of the present invention need only be a one dimensional array in the direction of the longitudinal (z) axis of the patient, a two dimensional array or a plurality of two dimensional arrays could be used if required to more accurately measure the exact two or three dimensional shape and location of an aerated cavity inside a patient.

In operation, the transducer array will start monitoring the movement of the lung sinus: each transducer element will detect a change in impedance as the patient breathes. The output from the transducer array can be registered for later use or constantly fed to a monitor or device.

In a simple case the outputs from the transducer elements may be regarded as essentially digital—in simple terms the output from each may be regarded as either indicating air (above the diaphragm) or indicating tissue (on or below the diaphragm). These outputs may then be fed to a processor that determines the position of the "step" from one to the other. This will correspond to diaphragm position. An output may then be made on a display, for example as a numerical value on an arbitrary scale.

In a more sophisticated embodiment the measured acoustic impedance from each transducer element is used as an input to the processor. Impedance may then be processed as a function that varies with the z-direction. The impedance values may, for example, be plotted on a visual display and a curve fitted to them. The diaphragm position will correspond to the point of greatest gradient. This can either be determined visually by an operator or calculated and presented as a position-value.

Using this apparatus it is possible to monitor the position of the lung sinus and thereby the diaphragm with great accuracy in real time. Procedures such as lung biopsies may therefore be performed with greater ease.

Moreover, in the context of radiotherapy, the apparatus may be coupled to a source of radiation and be arranged to trigger that source to emit radiation when the diaphragm is at a specific position. In this way, the radiation need only be directed at the patient when it is directly focused on its target. In an alternative and particularly preferred form of the invention, the direction of the radiation beam may be controlled to follow the movement of the target based on the determined position of the diaphragm.

In one such embodiment, the location of the tumor is measured at several different levels of inspiration and the path of the tumor throughout a normal breathing cycle is calculated as a function of diaphragm position. The radiation source is mounted on a tracking device that is controlled by the control unit to direct the radiation towards the calculated position of the tumor based on the current measurement of diaphragm position.

Furthermore, the inventors have recognized that when monitoring the respiratory status of seriously ill patients, e.g. in the intensive care unit (ICU) it would be useful to measure the position of the diaphragm by means of the present invention. This would give important information about the quality of respiration that is not available with the techniques currently used in the ICU.

BRIEF DESCRIPTION OF THE DRAWINGS

A preferred embodiment of the present invention will now be described, by way of example only, with reference to the accompanying drawings in which:—

FIG. 6 shows a system for implementing the embodiment of FIG. 1 illustrating how the invention may be utilised.

DETAILED DESCRIPTION

For the sake of clarity, the present invention will now be described with reference to a CT guided puncture operation.

However, it will be understood that, as discussed above, embodiments of the invention can also be used in the fields of radiation therapy and other aspects of respiration monitoring.

Figure 1:
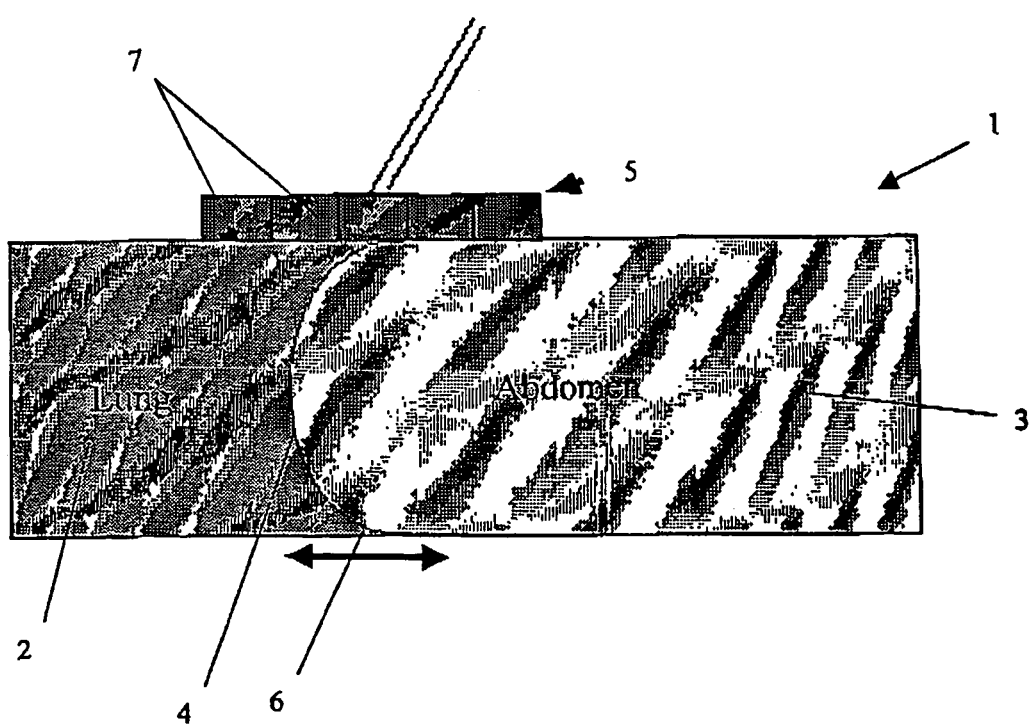
FIG. 1 shows a schematic representation of an embodiment of the invention using an array of ultrasound transducer elements to detect the location of a patient's diaphragm.

FIG. 1 shows a respiration monitoring apparatus in accordance with the present invention. A patient 1 having a lung 2 and an abdomen 3 being separated therefrom by a diaphragm 4 is fitted with an ultrasound transducer array 5 positioned approximately centrally over the lung sinus 6 prior to being given a CT or MRI scan. The transducer array 5 consists of a plurality or individual transducer elements 7 that span at least a part of the region of diaphragm movement i.e. from a relaxed state to a contracted state. In one embodiment, the transducer array is adapted to span the entire region of diaphragm movement. In alternative embodiments however, it can be adapted to span only 75%, 50% or 25% of the region of diaphragm movement respectively. In further possible embodiments, the array can be adapted to span from 1% to 15% or from 1% to 20% or from 1% to 25% of the region of diaphragm movement respectively. In a further possible alternative, the array consists of only one single ultrasound transducer element which is positioned at a particular point in the cycle of movement of the diaphragm in use.

Each individual transducer element 7 emits an ultrasound pulse and then detects its echo in the known manner. Because air has a much higher acoustic impedance than tissue, the reflection of the ultrasound beam is much more pronounced when the lung is insonated. Thus, the strength of signal received will be much higher when the pulse is reflected from an aerated space than when the pulse is reflected by tissue.

By measuring the strength of the receiving signal, i.e. the degree to which the transducers are receiving from air and from tissue, it is possible to determine to a high degree of accuracy the position of the patient's diaphragm.

In order to avoid interference between adjacent transducer elements, their pulses are phased so as not to occur simultaneously. However, because the duration of each pulse is very short, output that is effectively in real-time is produced.

Figure 2:
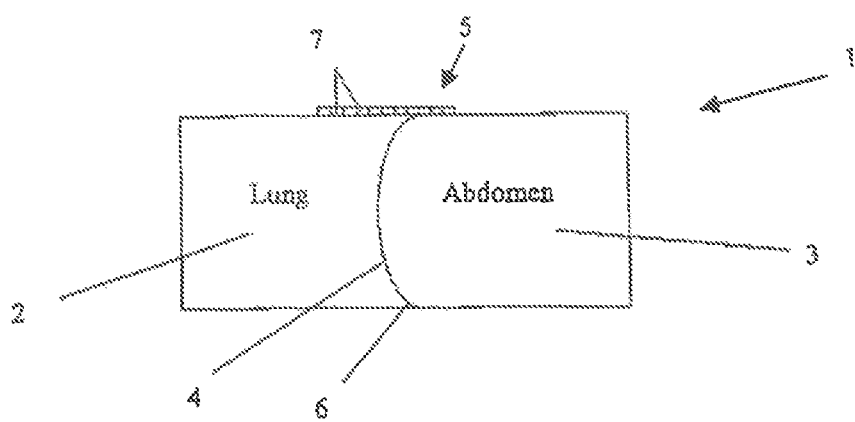
FIG. 2 shows the diaphragm in a contracted state (after inspiration)
Figure 3:
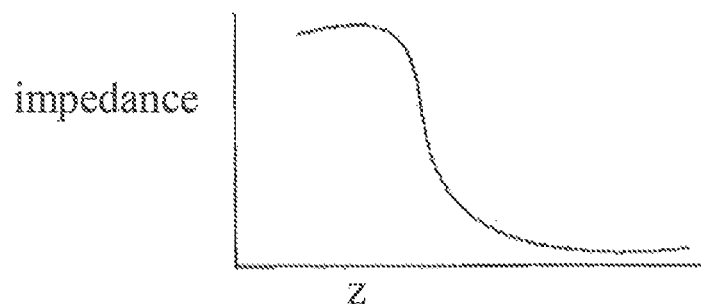
FIG. 3 illustrates output from the embodiment in the form of a graph illustrating acoustic impedance plotted against the z-direction with the diaphragm in a contracted state.
Figure 4:
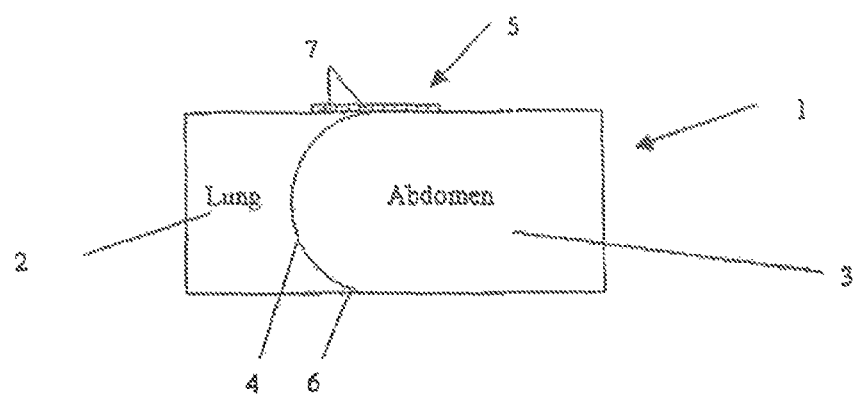
FIG. 4 corresponds to FIG. 2 but shows the diaphragm in a relaxed state (after expiration)
Figure 5:
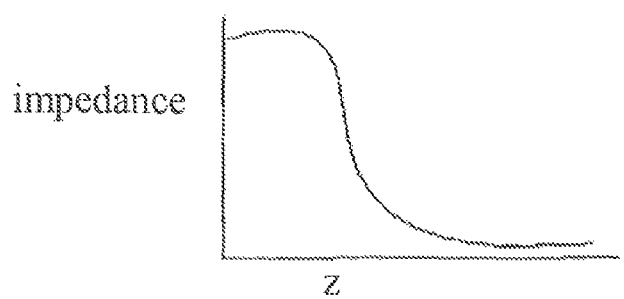
FIG. 5 corresponds to FIG. 3 but shows an impedance signal corresponding to the diaphragm state shown in FIG. 4.

As shown in FIG. 6, the measured acoustic impedance from each transducer element is used as an input to a processor 8. Impedance may then be processed as a function that varies in the z-direction. The impedance values are then plotted on a visual display 9 and a curve fitted to them. FIG. 3 illustrates a fitted curve for the position of the diaphragm as shown in FIG. 2 in a contracted state (after inspiration). FIG. 5 illustrates a fitted curve for the position of the diaphragm as shown in FIG. 4 in a relaxed stated (after expiration). The diaphragm position will correspond to the point of greatest gradient. This is calculated by the processor 8, highlighted on the display 9 and presented as a numerical position-value, also on the display 9.

After the patient 1 has been fitted with the transducer array 5, a CT or an MRI scan is performed on the patient to determine the precise location of the target (e.g. a lesion to be punctured). During the scan, the patient is required to hold his breath so that a clear image is produced with the lungs in one position. While the scan is being performed and while the patient is holding his or her breath, the exact position of the diaphragm is presented on the display and the position-value is noted.

The image from the scan is used to calculate the depth and angle at which a needle must be inserted for the lesion to be punctured. When the operator is ready to perform the puncture, the patient is asked to inhale until the display indicates that the diaphragm is in the same position as it was when the scan was performed. If the patient inhales too much and the transducer array indicates that the level of inspiration is greater than that held during the scan, the operator can instruct the patient to exhale a little. If necessary, the patient can relax and inhale again until the operator is happy with the position of the diaphragm.

In this way, the operator can be sure that the lesion is at the same position within the patient as it is shown in the CT or MR image while he or she performs the puncture. In the case of CT, the location of the needle may, however, still be checked by means of a further scan.

As described above, the apparatus of the present invention can also be used to improve radiotherapy treatments by reducing the area that needs to be irradiated. The basic procedure described above is employed, however, the embodiment is modified to provide a control output from the processor for controlling a source of radiation.

After the location of the tumor within the patient has been determined from the scan image, a radiation source is aimed at that location. This is connected to the control output such that the radiation source only emits when triggered to do so by the output signal from the processor.

The patient is allowed to breathe continuously throughout the radiation treatment. Meanwhile, the processor uses the outputs from the transducer array to continuously monitor the position of the diaphragm. When its position corresponds to the position that was determined during the scan, the processor sends a signal to trigger the radiation source to irradiate the target area of the patient. Thus, the area of the patient that needs to be irradiated can be significantly reduced because the location of the target can be determined to a much greater accuracy.

The invention claimed is:

1. A method of non-invasively detecting a position of a diaphragm of a patient comprising:
    placing over a lung sinus in the body of the patient an array of at least two ultrasound transducer elements extending in a direction of a longitudinal (z) axis of the patient;
    transmitting ultrasound signals into the body;
    receiving ultrasound signals reflected from the body; and
    non-invasively detecting a position of a diaphragm of the patient based upon a difference between the signals received by the individual transducer elements.

2. A method as claimed in claim 1, wherein the diaphragm position is used as a reference point to define the degree of lung inspiration when an image of the patient is generated and further comprising the step of reproducing that degree of lung inspiration in order to perform a medical or surgical procedure on the patient based on the image.

3. A method as claimed in claim 2, wherein the diaphragm position is first determined whilst the patient holds his breath and images are generated simultaneously therewith, the degree of lung inspiration subsequently being reproduced by the patient inhaling or inhaling and exhaling until the diaphragm position is achieved and the procedure being then carried out whilst the patient holds his breath.

4. The method of claim 2, wherein the medical or surgical procedure is a biopsy.

5. A method as claimed in claim 1, wherein the array of at least two ultrasound transducer elements is placed on the patient's lower chest and/or upper abdomen and is moved into a desired position over the lung sinus using feedback from the at least two ultrasound transducer elements.

6. The method of claim 1, further comprising:
    monitoring movement of the patient's diaphragm based on the detected position of the diaphragm; and
    monitoring respiration based on the monitored movement.

7. An apparatus for monitoring a position of a diaphragm of a patient comprising:
- an array of at least two ultrasound transducer elements for placing on the patient in the direction of a longitudinal (z) axis of the patient to extend over a lung sinus; and
- a controller configured to:
  - transmit ultrasound signals from the at least two transducer elements; and
  - determine the position of the diaphragm based upon a difference between signals received by each of the at least two ultrasound transducer elements.

8. An apparatus as claimed in claim 7, wherein a measured acoustic impedance from each of the at least two transducer elements is used as an input to a processor configured to process the acoustic impedance to provide a function that varies with movement of the diaphragm in the longitudinal (z) direction.

9. A method of radiotherapy comprising:
- providing a source of radiation;
- directing the source of radiation at a target area of a patient;
- monitoring a position of the patient's diaphragm using the apparatus according to claim 7; and
- triggering an emission of a radiation beam based upon the monitored diaphragm position.

10. A method of radiotherapy comprising:
- providing a source of radiation;
- directing a radiation beam from the source to a target area of a patient; and
- controlling an emission of the radiation beam to follow movement of the target based on a position of a diaphragm of the patient as determined by the method of determining lung inspiration of claim 1.

11. An apparatus for providing radiotherapy to a patient, comprising:
- a radiation source mounted on a tracking device;
- a processor for calculating a position of a tumor based on a current measurement of a position of a diaphragm of the patient obtained by the method of determining lung inspiration of claim 1; and
- a control unit for operating the tracking device to direct radiation of the source towards the calculated position of the tumor.

12. A method of radiotherapy comprising:
- providing a source of radiation;
- directing the source of radiation at a target area of a patient; and
- controlling an emission of a radiation beam to follow movement of the target based on a position of a diaphragm of the patient as determined by using the apparatus of claim 7.

13. A radiotherapy apparatus comprising a radiation source and a control unit, the source being mounted on a tracking device and being controlled by the control unit to direct radiation from the source towards a calculated position of a tumor based on a measurement of diaphragm position obtained by the apparatus of claim 7.

14. An apparatus as claimed in claim 7, wherein the array of at least two transducer elements is a one-dimensional array.

15. A method of monitoring respiration comprising:
- determining a position of a diaphragm of a patient using the apparatus of claim 7; and
- monitoring movement of the patient's diaphragm based on the determined position.

16. An apparatus for monitoring a diaphragm of a patient, the apparatus comprising:
- an array of at least two ultrasound transducer elements for placement on the patient in a direction of a longitudinal (z) axis of the patient to extend over a lung sinus,
  - each of the at least two transducer elements being configured to detect an ultrasound beam which is reflected from tissue adjacent to the transducer element and to provide an output signal; and
- a controller configured to:
  - measure the strength of each output signal to obtain a value for the acoustic impedance of the tissue adjacent to a respective transducer element; and
  - determine a position of the diaphragm based upon a comparison of the acoustic impedance values.

17. The apparatus of claim 16, wherein the array of at least two transducer elements is a one-dimensional array.

18. The apparatus of claim 16, wherein the measured acoustic impedance from each transducer element is used as an input to a processor configured to process the acoustic impedance measurements to provide a function that varies with movement of the diaphragm in the z-direction.

19. The apparatus of claim 16, wherein the controller is further configured to:
- monitor movement of the patient's diaphragm based on the determined position; and
- monitor respiration based on the monitored movement.

20. A radiotherapy apparatus comprising:
- a radiation source;
- a control unit; and
- an apparatus for monitoring diaphragm position as claimed in claim 16,
- wherein the radiation source is mounted on a tracking device and the control unit is configured to control the source to direct radiation toward a calculated position of a tumor based on the position of the diaphragm.

* * * * *